United States Patent [19]

Chopdekar et al.

[11] 4,045,494

[45] Aug. 30, 1977

[54] METHOD FOR PREPARING TRIOGRANOPHOSPHINES

[75] Inventors: Vilas M. Chopdekar, Parlin; William R. Davis, South Plainfield, both of N.J.

[73] Assignee: M&T Chemicals Inc., Greenwich, Conn.

[21] Appl. No.: 556,010

[22] Filed: Mar. 6, 1975

[51] Int. Cl.$^2$ .............................................. C07F 9/50
[52] U.S. Cl. ............................................ 260/606.5 P
[58] Field of Search .................................. 260/606.5

[56] References Cited

U.S. PATENT DOCUMENTS

| 2,913,498 | 11/1959 | Ramsden | 260/606.5 P |
| 3,414,625 | 12/1968 | Natoli et al. | 260/606.5 P |
| 3,499,039 | 3/1970 | Lorenz et al. | 260/606.5 P |

Primary Examiner—Helen M. S. Sneed
Attorney, Agent, or Firm—Robert P. Auber; Kenneth G. Wheeless; Robert Spector

[57] ABSTRACT

Triorganophosphines are prepared in high yield and purity by the simultaneous addition of an organomagnesium halide and a phosphorus trihalide to a reaction mixture in a 3:1 molar ratio, respectively. The reaction mixture also contains a linear ether or a heterocyclic ether wherein the ring contains 5 or 6 atoms.

4 Claims, No Drawings

METHOD FOR PREPARING TRIOGRANOPHOSPHINES

BACKGROUND

This invention relates to the preparation of triorganophosphines by reacting an organomagnesium halide with a phosphorus trihalide. This invention further relates to a method for preparing triorganophosphines in a higher yield and purity than can be achieved using procedures disclosed in the prior art.

U.S. Pat. No. 2,913,498 teaches that triorganophosphines can be obtained by reacting an excess of an arylmagnesium halide complex with a phosphorus trihalide. The arylmagnesium halide is present in the form of a complex with specified cyclic ethers. All of the examples in the patent disclose forming a triorganophosphine by the gradual addition of a phosphorus trihalide to a vessel containing an arylmagnesium chloride. This method of combining the two reagents is often less than satisfactory in that total product yield is relatively low and may contain 90% or less of the desired triarylphosphine. One explanation for this phenomenon may reside in the abnormally high viscosity of a reaction mixture containing a large excess of the arylmagnesium halide-ether complex, a triarylphosphine and the magnesium halide produced as a by product of the reaction. The high viscosity may impede proper mass and heat transfer, resulting in lower yields and formation of undesirable by-products.

It has now been found that these shortcomings of the prior art method can be eliminated or at least considerably reduced if the organomagnesium halide and the phosphorus trihalide are added to the reaction mixture simultaneously and in the required stoichiometric ratio of 3:1, respectively.

SUMMARY OF THE INVENTION

The present invention provides an improved method for preparing triorganophosphines of the general formula $R_3P$ where R represents an alkyl group containing between 1 and 16 carbon atoms, a cycloalkyl, aryl, alkaryl or aralkyl group, the alkyl residue of said aralkyl or alkaryl radical containing between 1 and 16 carbon atoms, the method comprising the steps of 1. adding to a reaction zone an organomagnesium halide of the formula RMgX and a phosphorus trihalide $PX_3$ such that 3 moles of RMgX are added separately and concurrently with each mole of $PX_3$
2. maintaining the resultant mixture at a temperature of between ambient and the boiling point of said mixture and
3. isolating the triorganophosphine.

The organomagnesium halide is present as a complex with a linear or cyclic ether. Cyclic ethers contain 5 or 6 atoms in the ring, one of which is oxygen. In the foregoing formulae X represents chlorine, bromine or iodine.

DETAILED DESCRIPTION OF THE INVENTION

The organomagnesium halide, RMgX, which is reacted with a phosphorus trihalide to form the corresponding triorganophosphine can be prepared by reacting an organic halide with magnesium metal in accordance with the equation

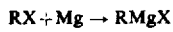

The reaction is carried out under an inert atmosphere, such as dry nitrogen, and in the presence of a linear ether or a cyclic ether containing 5 or 6 atoms in the ring, one of which is oxygen. The ether is believed to form a complex with the organomagnesium halide. Various initiators, including ethyl bromide, may be present to facilitate the reaction.

Suitable linear ethers are of the general formula $R^1OR^2$, wherein $R^1$ and $R^2$ each contain between 1 and 6 carbon atoms and are selected from the group consisting of alkyl, cycloalkyl and phenyl groups, with the proviso that $R^1$ and $R^2$ cannot both be methyl, cycloalkyl or phenyl.

The aforementioned class of cyclic ethers exhibits the general formula

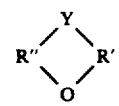

R' is a methylene or an ethylene group or a group of the formula =CHR''', wherein R''' is an alkyl group containing between 1 and 16 carbon atoms, R'' is an unsubstituted alkylene group such that R' and R'' together contain 3 or 4 cyclic carbon atoms, which together with the oxygen and Y groups form a ring containing 5 or 6 atoms and Y is a methylene or an N-alkyl group,

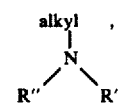

containing between 1 and 16 carbon atoms, with the proviso that when Y represents an N-alkyl group, the Y and O groups are separated by 2 atoms and the ring contains 6 atoms.

Cyclic ethers within this definition include tetrahydrofuran, tetrahydropyran, 2-methyltetrahydrofuran, 2-ethoxytetrahydropyran, tetrahydrofurfurylethyl ether, dihydropyran, and N-methylmorpholine. The ether may bear inert groups i.e. groups which are not reactive with organomagnesium halides, or with any of the components and products of the reaction mixtures of the present process. Illustrative inert substituents may include substituted and unsubstituted alkyl, aryl, alkoxy, and aryloxy groups (including those bearing substituents thereon which are unreactive with other components of the reaction mixture as herein specified). Where nitrogen replaces a carbon atom in the ring at X, the nitrogen atom must be substituted with a group, such as an alkyl group, which is unreactive to the reactants or reaction products.

It is characteristic of the present linear and cyclic ethers that the oxygen is available for electron donation, i.e. the free π-electrons present on the oxygen are available for coordination with the Grignard reagent. Any large blocking groups on the carbon atoms adjacent to the oxygen atoms may impair the availability of these electrons and the reactivity of the compound for forming a complex and assisting in the reaction. In addition to the cyclic ethers listed above, equivalent linear compounds satisfying the foregoing requirements will be apparent to those skilled in the art from the present specification. Oligomeric polyethers of the general formula $R^3(OR^4)_nOR^3$ wherein $R^3$ is alkyl and contains 2, 3 or 4 carbon atoms, $R^4$ is alkylene and contains 2, 3 or 4 carbon atoms and $n$ is between 1 and 4, inclusive, are also suitable complexing agents. Since the ether may also function as a solvent for the reaction with the phosphorus trihalide, an ether which has a relatively high melting point may be used in practice of this invention, but if it is used as solvent, the high melting point (e.g. above 90° C.) may cause difficulty in carrying out the reaction.

The organomagnesium compound formed in accordance with the foregoing equation may preferably be in the form of a solution of its complex with the ether. For purpose of convenience, the equations and formulae herein are written without reference to the ether.

The organomagnesium halide and/or the reaction mixture may preferably also contain an inert hydrocarbon in addition to the ether.

The reaction between the organomagnesium halide and the phosphorus trihalide is achieved by adding the two reagents separately to a vessel or other suitable reaction zone equipped with an efficient stirrer. The reaction vessel preferably initially contains a small amount of the aforementioned cyclic ether. The rate of addition of the two reagents is such that three moles of the organomagnesium halide are added for every mole of the phosphorus trihalide. It has been found that up to 4.5 moles of halide (i.e. a 50% excess of the stoichiometric amount) can be present in the reaction vessel for each mole of the phosphorus trihalide without any significant adverse effect on product purity or yield.

Depending upon the desired triorganophosphine, the hydrocarbon group of the organomagnesium halide can be an alkyl group containing between 1 and 16 carbon atoms, a cycloalkyl, aryl, alkaryl or aralkyl group wherein the alkyl residue of the alkaryl or aralkyl group contains between 1 and 16 carbon atoms. Representative aliphatic hydrocarbon groups include methyl, ethyl, n-propyl, iso-propyl, n-butyl, sec-butyl, t-butyl and n-hexyl, in addition to the isomeric heptyl, octyl, decyl, dodecyl and hexadecyl groups. Suitable cycloaliphatic groups are represented by cyclohexyl and cyclopentyl. Phenyl and naphthyl are representative of the useful aryl groups. Aralkyl groups within the present invention include benzyl and $\beta$-phenylethyl. Suitable alkaryl groups include tolyl, xylyl and p-ethylphenyl.

The temperature of the mixture resulting from the concurrent additions of the organomagnesium halide and phosphorus trihalide to the reaction zone is between ambient and the boiling point of the reaction mixture. This temperature is maintained throughout the addition of the two reagents and preferably for about one and three hours following completion of the addition to ensure completeness of the reaction and maximum product yield. The resultant mixture should be thoroughly agitated throughout this period to facilitate heat transfer and sufficient contact between molecules of the two reactive species.

Since the organomagnesium halide reacts with even trace amounts of moisture, the reaction zone preferably contains a dry, inert atmosphere such as nitrogen.

The present method is suitable for a continuous process whereby the two reactants are introduced simultaneously and continuously into a reaction zone maintained at a temperature between ambient and the boiling point of the reaction mixture. As the reaction product forms, it is continuously removed and hydrolyzed to yield an organic layer containing the desired triorganophosphine and the ether with which the aforementioned Grignard reagent is complexed and an aqueous layer containing a solubilized magnesium halide.

The desired triorganophosphine is isolated from the reaction mixture by hydrolysis using an aqueous solution of an acidic electrolyte such as a non-oxidizing mineral or carboxylic acid. Suitable acids include sulfuric, hydrochloric, formic, acetic and oxalic acids. The amount of acid added is sufficient to achieve a pH lower than 7. The acidic medium decomposes the intermediate complex present in the reaction mixture to form the desired triorganophosphine together with a magnesium halide salt. The latter dissolves in the aqueous layer of the two phase liquid formed during the hydrolysis, and is readily removed by decantation. The triorganophosphine is readily isolated by removing a portion or all of the ether from the organic layer. Many of the triarylphosphines are solid materials and can be recrystallized as required to achieve the desired purity. The trialkylphosphines, particularly those containing a total of less than 21 carbon atoms are liquids that can be purified by distillation under ambient or reduced pressure as is well known in the art.

By adding the organomagnesium halide and the phosphorus trihalide concurrently as taught in the foregoing specification and accompanying examples it is possible to obtain crude product yields in excess of 90%. In addition, the amount of the corresponding triorganophosphine oxide, a by-product of the reaction, is significantly reduced relative to the amount obtained using prior art methods whereby the phosphorus trihalide is gradually added to the organomagnesium halide.

The following examples demonstrate preferred embodiments of the present method and should not be interpreted as limiting the scope thereof as defined in the accompanying claims. All parts and percentages are by weight unless otherwise specified.

EXAMPLE 1

A one liter-capacity reaction vessel equipped with a mechanically driven agitator, water-cooled reflux condenser, two pressure equalized addition funnels, thermometer and a nitrogen inlet was charged with 10 g. of anhydrous tetrahydrofuran. One of the addition funnels contained 272 g. of a tetrahydrofuran solution containing 0.847 mole of phenyl magnesium chloride and the second funnel contained 34.3 g. (0.25 mole) of phosphorus trichloride. The two reagents were added to the reaction vessel over a 2 hour period, the relative addition rates being adjusted such that 3 moles of phenyl magnesium chloride were added for every mole of phosphorus trichloride. The temperature of the reaction mixture was maintained at between 60° and 65° C. and the mixture was stirred throughout the addition of the two reagents and for one-half hour thereafter. The reaction mixture was then heated to reflux temperature for 1 hour, after which it was allowed to cool to ambient temperature and hydrolyzed by the addition of a dilute, aqueous solution of sulfuric acid (5 g. $H_2SO_4$ and 205 g. water). After being stirred for one-half hour at ambient temperature the aqueous and organic liquid phases were separated and the organic layer analyzed by vapor phase chromatography (V.P.C.). Tetrahydrofuran was removed from the organic phase under reduced pressure and the resultant solid recrystallized using methanol. The recrystallized solid was dried and analyzed to determine purity (i.e. % of triphenylphosphine).

Triphenylphosphine (TPP) was also prepared using the method taught by Ramsden in U.S. Pat. No. 2,913,498. In this instance the reaction vessel contained the entire amount of phenyl magnesium chloride dissolved in tetrahydrofuran to which phosphorus trichloride was added over a period of two hours. Following completion of the addition the procedure was substantially identical to that specified hereinabove for the simultaneous addition method. This procedure was repeated once to ensure reproducibility.

Analytical data for the crude and recrystallized materials are summarized in the accompanying table.

| Method of Reagent Addition | V.P.C. Analysis of Crude Product (%) | | | % TPP in Recrystallized Product | % Yield (Recrystallized) |
| --- | --- | --- | --- | --- | --- |
| | Low Boiling Materials | Triphenyl Phosphine | Triphenyl Phosphine Oxide | | |
| Simultaneous | 4.9 | 91.5 | 3.6 | 99.9 | 90.0 |
| Simultaneous | 1.73 | 94.58 | 2.75 | 100 | 93.9 |
| Simultaneous | 4.2 | 92.5 | 3.4 | 99.3 | 92.1 |
| Prior Art | 6.4 | 88.6 | 5.1 | 99.5 | 86.8 |
| Prior Art | 4.59 | 89.22 | 5.44 | 100 | 88.3 |

What is claimed is:

1. A method for preparing a triorganophosphine, said method comprising the steps of
   1. adding to a reaction zone maintained under an inert atmosphere an organomagnesium halide of the formula RMgX and a phosphorus trihalide $PX_3$ such that three moles of the organomagnesium halide are added separately and concurrently with each mole of the phosphorus trihalide, wherein said reaction zone also contains either a linear ether of the formula $R^1OR^2$ or $R^3(OR^4)_nOR^3$ or a cyclic ether of the general formula

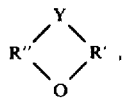

wherein R represents an alkyl group containing between 1 and 16 carbon atoms, a cycloalkyl, aryl, alkaryl or aralkyl group such that the alkyl portion of said alkaryl or aralkyl group contains between 1 and 16 carbon atoms, $R^1$ and $R^2$ each contain between 1 and 6 carbon atoms and are individually selected from the group consisting of alkyl, cycloalkyl and phenyl with the proviso that $R^1$ and $R^2$ cannot both be methyl, cycloalkyl or phenyl, $R^3$ is alkyl and contains 2, 3 or 4 carbon atoms, $R^4$ is alkylene and contains 2, 3 or 4 carbon atoms, R' is methylene, ethylene or $=CHR'''$, wherein R''' is alkyl and contains between 1 and 16 carbon atoms, R'' is unsubstituted alkylene such that R' and R'' together contain 3 or 4 cyclic carbon atoms, and together with the oxygen atom and Y group form a ring containing 5 or 6 atoms, n is between 1 and 4, inclusive, X is chlorine, bromine or iodine and Y is a methylene or an N-alkyl group containing between 1 and 16 carbon atoms, with the proviso that when Y represents an N-alkyl group, the Y group and the oxygen atom are separated by 2 atoms and said ring contains 6 atoms,
   2. maintaining said reaction zone at a temperature of between ambient and the boiling point of the reaction mixture throughout the addition of the organomagnesium halide and phosphorus trihalide,
   3. adjusting the pH of the reaction mixture to less than 7 by the addition of an aqueous solution containing a non-oxidizing mineral or carboxylic acid,
   4. removing the aqueous layer of the reaction mixture, and
   5. removing at least a portion of the solvent from the organic layer of the reaction mixture to isolate the resultant triorganophosphine, $R_3P$.

2. A method for preparing a triorganophosphine as described in claim 1 wherein R is a phenyl radical and X is chlorine.

3. A method for preparing a triorganophosphine as described in claim 1 wherein the ether is a cyclic ether.

4. A method for preparing a triorganophosphine as described in claim 3 wherein said cyclic ether is tetrahydrofuran.

* * * * *